United States Patent [19]

Barnes et al.

[11] Patent Number: 4,721,723

[45] Date of Patent: Jan. 26, 1988

[54] ANTI-DEPRESSANT CRYSTALLINE PAROXETINE HYDROCHLORIDE HEMIHYDRATE

[75] Inventors: Roger D. Barnes, Betchworth; Marian W. Wood-Kaczmar, Harlow; Alan D. Curzons, Worthing; Ian R. Lynch, Epsom; John E. Richardson, Harlow; Philip C. Buxton, Epsom, all of England

[73] Assignee: Beecham Group p.l.c., Brentford, England

[21] Appl. No.: 922,530

[22] Filed: Oct. 23, 1986

[30] Foreign Application Priority Data

Oct. 25, 1985 [GB] United Kingdom ............... 8526407
Oct. 25, 1985 [GB] United Kingdom ............... 8526408

[51] Int. Cl.$^4$ ............... A61K 31/445; C07D 405/12
[52] U.S. Cl. .......................... 514/321; 546/197
[58] Field of Search ..................... 546/197; 514/321

[56] References Cited

U.S. PATENT DOCUMENTS 4,007,196 2/1977 Christensen ................... 546/197

OTHER PUBLICATIONS

*Chemical Abstracts,* 95:54664z (1981) [Goethert, M., et al., *Naunyn-Schmiedeberg's Arch. Pharmacol.* 1980, 313(1), 21–6].
J. B. Lassen, *Psychopharmacology,* 57, pp. 151–153 (1978).
J. B. Lassen, *European J. Pharmacol.,* 47, pp. 351–358 *(1978).*
J. Lund et al., *Acta Pharmacol. et Toxicol.,* 44, pp. 289–295 (1979).
J. B. Lassen, et al., *Psychopharmacology,* 68, pp. 229–233 (1980).

*Primary Examiner*—Richard A. Schwartz
*Attorney, Agent, or Firm*—James F. Haley, Jr.; Alan M. Gordon

[57] ABSTRACT

The invention provides crystalline paroxetine hydrochloride hemihydrate, processes for its preparation, compositions containing the same and its therapeutic use as an anti-depressant.

6 Claims, 3 Drawing Figures

Fig.2

Fig. 3

ANTI-DEPRESSANT CRYSTALLINE PAROXETINE HYDROCHLORIDE HEMIHYDRATE

This invention relates to crystalline paroxetine hydrochloride, its preparation and its use as a therapeutic agent.

U.S. Pat. No. 4,007,196 discloses a class of compounds that are inhibitors of 5-hydroxytryptamine (5HT) uptake and thus of therapeutic use as anti-depressants. In Example 2 of the U.S. patent there is described the preparation of (−)-trans-4-(4'-fluorophenyl) 3-(3'4'-methylenedioxyphenoxymethyl)-piperidine of formula A:

In this specification the compound of formula A is referred to by its generic name of paroxetine.

Because of its basicity, it is preferred that paroxetine is used as a therapeutic agent in the form of an acid addition salt. In Example 2 of U.S. Pat. No. 4,007,196, paroxetine is obtained as the free base and then converted to its maleic acid salt.

The acetate salt of paroxetine has been used in most of the published experimental trials [for example, *Psychopharmacology*, 57, 151–153 (1978); *ibid.* 68, 229–233 (1980); and *European Journal of Pharmacology*, 47 (1978) 351–358]. There has also been limited use of the hydrochloride salt (in aqueous solution) [*Acta. Pharmacol. et Toxicol.* 1979, 44, 289–295]. However, the preparation of paroxetine hydrochloride has not been described in the literature.

In general, the hydrochloride salt of a basic compound is preferred for therapeutic use because of its physiological acceptability.

However for commercial use it is also important that the solid product should have good handling qualities.

We have found that amorphous paroxetine hydrochloride is a hygroscopic solid of poor handling qualities.

It has now been discovered that paroxetine hydrochloride can be produced in crystalline form in a manner reproducible on a commercial scale.

The present invention provides crystalline paroxetine hydrochloride hemihydrate as a novel material, in particular in pharmaceutically acceptable form.

Figure 1:
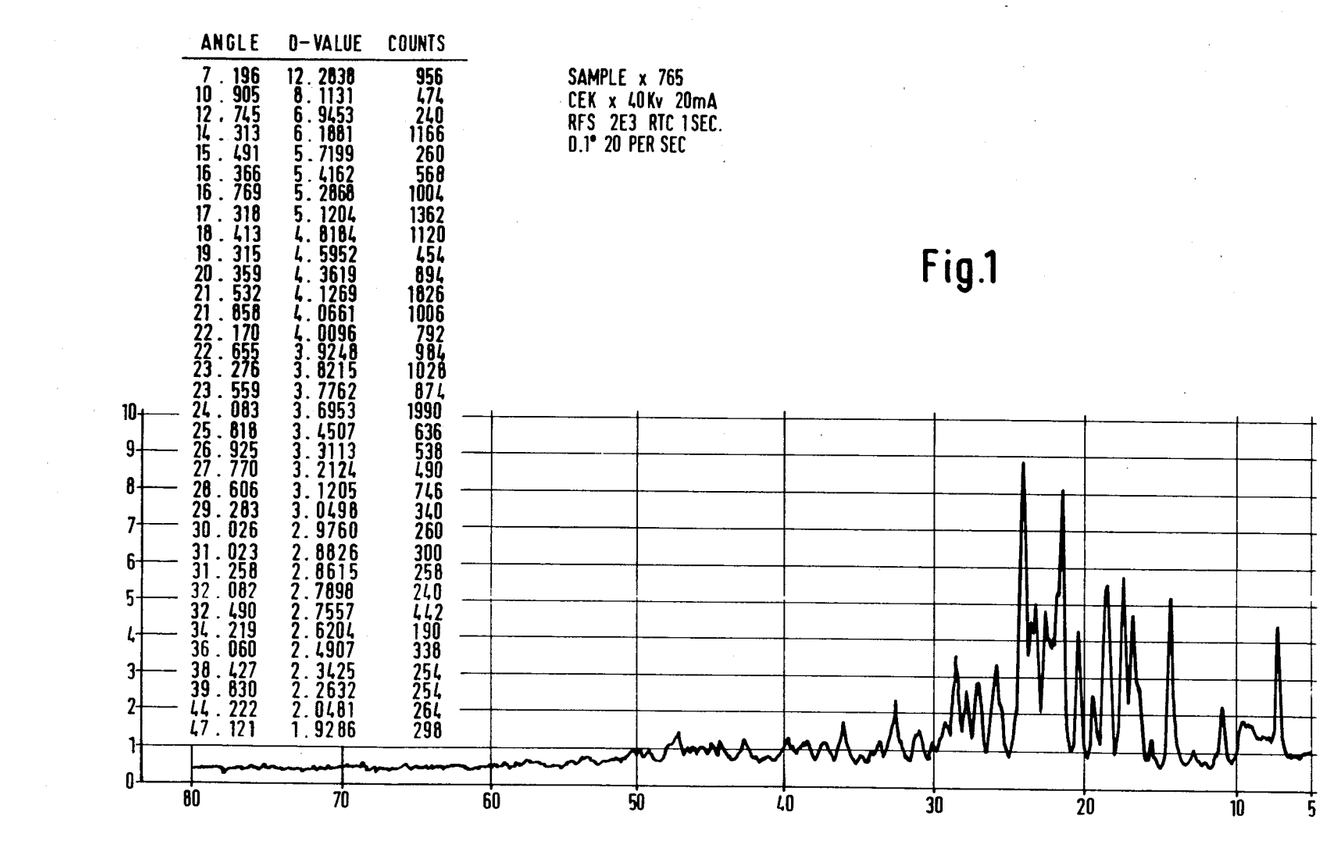
Figure 2:
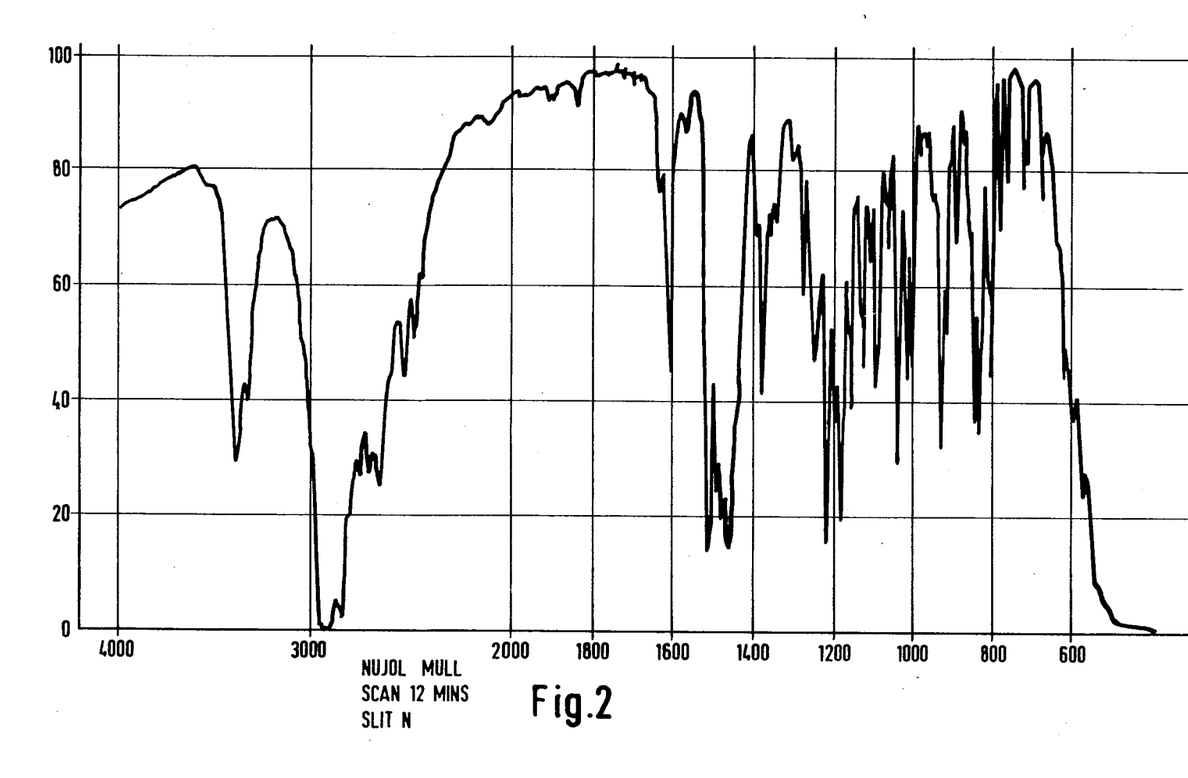
Figure 3:
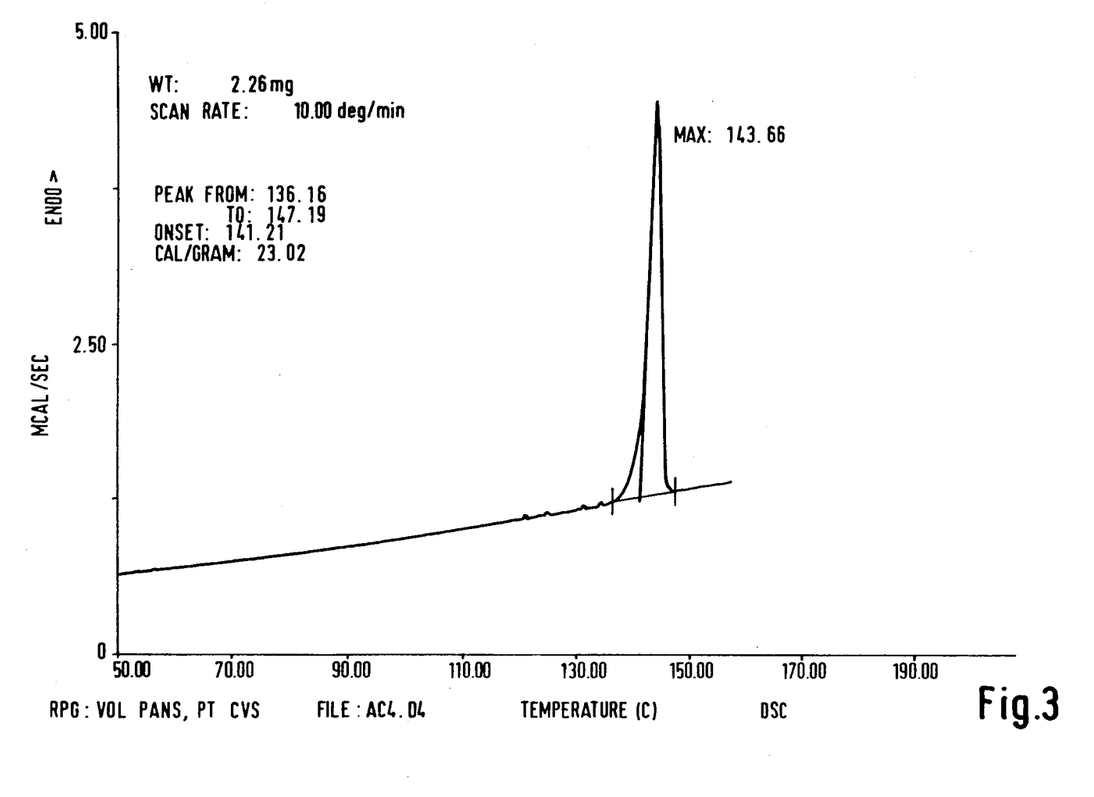

Paroxetine hydrochloride hemihydrate is stable and non-hygroscopic. It is characterised by an X-ray powder diffractogram as shown in the accompanying FIG. 1. A typical Nujol infra-red spectrum (FIG. 2) and DSC profile (prepared using a 2.26 mg sample in a sealed container (FIG. 3) is also shown. Under extreme dessication conditions the bound water may be removed to give an anhydrous form, but on rehydration it rapidly reforms the hemihydrate.

The present invention also provides a process for producing crystalline paroxetine hydrochloride hemihydrate which comprises forming a solution of paroxetine hydrochloride and precipitating the crystalline form from solution.

The solution may be formed by dissolution of preformed paroxetine hydrochloride or by forming the hydrochloride in situ. The hydrochloride may be formed from a solution of paroxetine free base or a salt other than the hydrochloride by contacting it with hydrogen chloride.

For example a solution of hydrogen chloride, for example concentrated hydrochloric acid or an organic solvent saturated with hydrogen chloride may be added to a solution of paroxetine salt. Alternatively hydrogen chloride gas may be passed through the paroxetine (salt) solution.

Paroxetine base may be prepared by the procedure disclosed in U.S. Pat. No. 4,007,196. The U.S. Patent also gives procedures for preparing salts of paroxetine with various organic acids.

Typically, paroxetine hydrochloride may be obtained from an organic solution e.g. in toluene, of the free base by adding an appropiate amount of aqueous HCl.

In a procedure using a salt, paroxetine hydrochloride may be produced from a paroxetine $C_{1-5}$ carboxylate such as the acetate. The acetate may be obtained by reaction of acetic acid and paroxetine base in a nonpolar solvent, such as diethyl ether or isopropyl ether. Alternatively it may be obtained from an aqueous solution obtained by extraction from a water-immiscible solvent e.g. toluene, ethyl acetate, by the addition of water and an appropriate amount of acetic acid.

Before conversion to the hydrochloride or crystallisation it may be desirable to remove impurities, since it has been found that some impurities may act as crystallisation inhibitors. However, the hemihydrate can even be obtained from relatively impure starting material, by means of seeding.

Paroxetine hydrochloride may be obtained as a crystalline hemihydrate by crystallization after addition of an aqueous solution of hydrochloric acid to a solution of paroxetine free base in water immiscible solvents e.g. toluene, or by crystallisation from water miscible solvents which do not form a solvate (e.g. IMS) after adding aqueous hydrochloric acid to a solution of the free base or by crystallising or recrystallising paroxetine hydrochloride from a solvent system containing water e.g. IMS/water. Alternatively the hydrochloride hemihydrate can be produced via another paroxetine salt by the addition of hydrochloric acid to an aqueous solution of the salt e.g. acetate.

In a preferred aspect, this invention provides paroxetine hydrochloride hemihydrate which is substantially pure.

The hemihydrate can be obtained by crystallisation from a range of solvents, although seeding may be necessary in some instances, after addition of aqueous HCl to a solution of the free base or another salt. Solvents which have been found suitable are toluene, water, IMS, lower alcohols such as ethanol and isopropanol and ethyl acetate. The same solvent range may be used for recrystallizatation.

In a particular aspect of the invention, paroxetine free base is synthesised in a particularly pure form which is especially suitable for use in the preparation of the crystalline paroxetine hydrochloride hemihydrate of the invention, even without seeding.

In the above mentioned U.S. Pat. No. 4,007,196, for the preparation of paroxetine (Examples 1 and 2), an N-methyl compound is reacted with phenyl chloroformate and the resultant compound is hydrolysed with potassium hydroxide.

One disadvantage of this process is that the solvent used during the hydrolysis step (methyl cellosolve) leads to the production of unwanted transesterification by-products.

We have now discovered that the purity of the final product can be improved by using a different solvent during the hydrolysis step, such as toluene. A further advantage is that the temperature at which the hydrolysis is carried out can thus be reduced, owing to the reduction in boiling point of the solvent used.

The pure paroxetine free base thus obtained can then be used for the preparation of crystalline paroxetine hydrochloride hemihydrate as set out above.

In a further aspect of the invention, crystalline paroxetine hydrochloride hemihydrate can be obtained by compressing crystalline paroxetine hydrochloride anhydrate.

In a still further particular aspect of the invention, paroxetine is synthesised directly as its hydrochloride salt, followed by crystallization as set out above.

We have discovered a new process for the preparation of paroxetine and related compounds by a de-acylation procedure which advantageously provides the desirable hydrochloride salt directly.

Accordingly, the present invention provides a process for the preparation of a compound of formula I in which $R^2$ represents an alkyl or alkynyl group having 1–4 carbon atoms, or a phenyl group optionally substituted by $C_{1-4}$ alkyl, $C_{1-6}$ alkylthio, $C_{1-6}$ alkoxy, halogen, nitro, acylamino, methylsulfonyl or methylenedioxy, or represents tetrahydronaphthyl, and X represents hydrogen, alkyl having 1–4 carbon atoms, $C_{1-6}$ alkoxy, $C_{1-6}$ trifluoroalkyl (preferably, trifluoromethyl), hydroxy, halogen, methylthio, or aryl($C_{1-6}$)alkyloxy (e.g., phenyl($C_{1-6}$)alkyloxy and benzyl($C_{1-6}$)alkyloxy) by de-acylating a compound of formula II in which $R^1$ is a $C_{1-6}$ alkyl group and X is as defined for formula I.

The de-acylation may be achieved by heating the compound of formula II in a lower alcohol e.g. methanol. Preferably $R^1$ is a methyl group.

The de-acylation is advantageously carried out as the final step of a procedure for de-alkylating a compound of formula III in which $R^3$ is a $C_{1-6}$ alkyl group and X is as defined for formula I.

The replacement of $R^3$ by $R^1.CHClO.CO$ to convert the compound of formula III to the compound of formula II may be achieved by reacting the compound of formula III with α-chloro-ethyl chloroformate in a solvent such as dichloroethane or toluene.

Alternatively, the compound of formula III may be reacted with vinyl chloroformate in a solvent such as methylene dichloride or toluene to obtain the intermediate of formula IV wherein X and $R^2$ are as defined for formula I, which is then treated with HCl, preferably by passing HCl gas through the solution to obtain the compound of formula II.

An advantageous feature of this process is that the conversion of the compound of formula III into the compound of formula I can be carried out as a 'one-pot' process without isolating the intermediate of formula II or the intermediate of formula IV if the alternative route is followed.

The compounds of formula III may be prepared by the procedures set out in U.S. Pat. No. 4,007,196.

Advantageously, the process is used for the de-alkylation of a compound of formula IIIa to obtain paroxetine hyrochloride of formula Ia. This procedure is illustrated in the following reaction scheme.

The intermediates having the general formulae II and IV given above are novel compounds. They form part of the present invention, together with the processes for their preparation described herein. Compounds of formula I, which include paroxetine hydrochloride, are useful as antidepressants, as disclosed in U.S. Pat. No. 4,007,196, the disclosure of which is hereby incorporated herein by reference. In its preferred aspect the present invention provides paroxetine hydrochloride hemihydrate in pharmaceutically acceptable form.

The present invention also provides a pharmaceutical composition comprising crystalline paroxetine hydrochloride hemihydrate and a pharmaceutically acceptable carrier.

The compositions of this invention are usually adapted for oral administration, but formulations for dissolution for parenteral administration are also within the scope of this invention.

The composition is usually presented as a unit dose composition containing from 1 to 200 mg, more usually from 5 to 100 mg, for example 10 to 50 mg such as 12.5, 15, 20, 25 or 30 mg. Such composition is normally taken from 1 to 6 times daily, for example 2, 3 or 4 times daily so that the total amount of active agent administered is within the range 5 to 400 mg.

Preferred unit dosage forms include tablets or capsules.

The composition of this invention may be formulated by conventional methods of admixture such as blending, filling and compressing.

Suitable carriers for use in this invention include a diluent, a binder, a disintegrant, a colouring agent, a flavouring agent and/or a preservative. These agents may be utilized in conventional manner, for example in a manner similar to that already used for clinically used anti-depressant agents.

The invention also provides a method of treatment of depression in mammals including humans which method comprises administering an effective amount of pharmaceutically acceptable crystalline paroxetine hydrochloride hemihydrate.

The invention further provides pharmaceutically acceptable crystalline paroxetine hydrochloride hemihydrate for use in the treatment of depression.

The following Examples illustrate the invention. Examples 4 and 5 show the route formula III-IV-II-I, while Examples 6 and 7 show the route formula III-II-I. Temperatures are in ° C.

EXAMPLE 1

(—)trans-4-(4'-Fluorophenyl)-3-(3'4'-methylenedioxyphenoxymethyl)-piperidine hydrochloride (Paroxetine hydrochloride) as hemihydrate (½H₂O)

(—)trans-4-(4'-Fluorophenyl)-3-(3'4'-methylenedioxyphenoxymethyl)-N-phenoxycarbonylpiperidine (18.5gms) was dissolved in toluene(275 mls). Potassium hydroxide (15.7 gms) was added. The mixture was refluxed for 2 hours with good agitation. The slurry was then cooled to 20° C. and the toluene washed once with water (275 mls).

To a solution of 13.5 g Paroxetine free base in toluene(300 ml) was added a small excess of either concentrated hydrochloric acid(5.2 ml)or dilute hyirochloric acid (150 mls of 0.35N)

The slurry was stirred at ambient temperature for 2 hours. The product was washed with toluene/water(25 ml 1:1 mixture) and dried at 50° C. to give paroxetine hydrochloride as the hemihydrate (½H₂O) containing 2.5% H₂O with m.p. 128°-133° C., and IR consistent with that shown in FIG. 2.

EXAMPLE 2

(−)trans-4-(4'-Fluorophenyl)-3-(3'4'-methylenedioxy-phenoxymethyl)piperidine hydrochloride (Paroxetine hydrochloride) as hemihydrate (½H₂O)

To a solution of paroxetine free base obtained as described in Example 1 [23.5g] in toluene (ca.500 ml) was added 300 ml water. Acetic acid was added (6.4 g) and after 15 minutes stirring the lower aqueous layer containing paroxetine acetate was separated.

The aqueous layer was clarified by filtration through celite. Concentrated hydrochloric acid (15. Oml) was then added at ambient temperatures in the presence of paroxetine hydrochloride seed obtained as in Example 1 and the precipitated product stirred for 1 hour at ambient and then 2 hours at 0°-5° C.

The product was filtered, washed with water (2x40 ml)and dried at 50° C. to give paroxetine hydrochloride hemihydrate containing 2.6% H₂O and consistent IR.

EXAMPLE 3

Recrystallisation of Paroxetine hydrochloride to give the hemihydrate (a) 0.50 g Paroxetine hydrochloride was recrystallised from 2.5 ml IMS (industrial methylated spirit) by dissolving at ca 60°-70° C. and cooling slowly to 20° C. then to 5° C. After seeding with crystals obtained as in Example 1, crystals of paroxetine hydrochloride hemihydrate were deposited and isolated in the normal way.

(b) 0.75 gm Paroxetine hydrochloride was recrystallised from 5. Oml water by dissolving at ca. 70° C. and cooling slowly to 20° C. After seeding with crystals obtained as in Example 1, crystals of paroxetine hydrochloride hemihydrate were deposited and isolated in the normal way.

EXAMPLE 4

(−)-trans-4-(4'-Fluorophenyl)-3-(3',4'-methylene-dioxyphenoxymethyl)-piperidine hydrochloride Vinyl chloroformate (6.42 ml) was dissolved in 2 ml dry methylene dichloride. The solution was cooled to 0° and the reaction flask purged with nitrogen. A solution of (−)-trans-4-(4'-fluorophenyl)-3-(3',4'methylene-dioxy-phenoxy) methyl-N-methyl- piperidine (20 g) in 52 ml of dry methylene dichloride was added to the vinyl chloroformate solution over 30 minutes keeping the temperature below 0°. The mixture was allowed to warm to ambient temperature and stirred for 3 hours. The solution was then heated to reflux at 35° for a further 1 hour and cooled to −20°. Dry hydrogen chloride gas was bubbled into the solution for about 1 hour and the mixture allowed to stir at ambient temperature for 1 hour. Methanol (50 ml) was added to the solution and the mixture heated under reflux for 1 hour, followed by addition of charcoal (4.5 g) to the hot solution. Charcoal was filtered off after 10 minutes and the solvents removed in vacuo to give the crude product (21.4 g). The solid was dissolved in isoprOpyl alcohol (140 ml) and the solution filtered. The clear filtrate was cooled to 0° and seeded with crystals obtained as in Example 1 to allow the product to crystallise. After several hours at 0° the white solid was filtered off and the product slurried in water (30 ml), filtered off, washed with water and dried to give the hydrochloride salt as the hemihydrate (15.8 g, 74.1%).

$^1$H—n.m.r. (270 MHz, DMSO—d₆)

| δ | Multiplicity | Assignment | |
|---|---|---|---|
| 9.50 | s, br, exch. | NH₂⁺ | 2H |
| 7.27 | dd, $^4J_{HF}$ = 6Hz | 2' | 2H |
| 7.17 | dd, $^3J_{HF}$ = 9Hz | 3' | 2H |
| 6.75 | d | 5" | 1H |
| 6.50 | d | 2" | 1H |
| 6.20 | dd | 6" | 1H |
| 5.94 | s | O—CH₂—O | 2H |
| 3.61 | dd | 7 | 2H |
| 3.53 | dd | | |
| 3.50 | m | 2 eq | 1H |
| 3.39 | d, br | 6 eq | 1H |
| 3.03 | ddd | 6 ax | 1H |
| 2.97 | dd | 2 ax | 1H |
| 2.90 | ddd | 4 | 1H |
| 2.58 | m | 3 | 1H |
| 2.10 | ddd | 5 ax | 1H |
| 1.85 | d, br | 5 eq | 1H |

EXAMPLE 5

(−)-trans-4-(4'-Fluorophenyl)-3-(3',4'-methylenedioxy-phenoxymethyl-piperidine hydrochloride The reaction described in Example 4 was repeated substituting 100 ml of sodium dried toluene for 52 ml of dry methylene chloride. (−)-trans-4-(4'-Fluorophenyl)-(3+,4'-methylenedioxyphenoxymethyl)-N-methyl-piperidine (20 g) was converted to 16.5 g of the hydrochloride salt as the hemihydrate in a yield of 77.4%.

The $^1$H-n.m.r. spectrum was identical to that of the Example 4 product.

EXAMPLE 6

(−)-trans-4-(4'-Fluorophenyl)-3-(3',4'methylenedioxy-phenoxymethyl)-piperidine hydrochloride (−)-trans-4-(4'-Fluorophenyl)-3-(3',4'-methylenedi-oxyphenoxymethyl)-N-methylpiperidine (10 g) and N,N,N',N'-tetramethyl-1,8-naphthalenediamine (0.3 g) were dissolved in 40 ml of dry 1,2-dichlorethane (EDC) and the solution cooled to −3°. α-Chloroethyl chloroformate (3.22 ml) in 5 ml of dry EDC was added to the cold solution over 15 minutes. The mixture was stirred for 20 hours at ambient temperature and then heated to reflux for 2 hours. Methanol (15 ml) was added to the solution and the mixture was refluxed for a further 2 hours. The mixture was washed with 20 ml of 1N hydrochloric acid and the phases were allowed to separate. The organic layer was evaporated to dryness and the residue was dissolved in isopropyl alcohol (60 ml). The hot solution was treated with charcoal (2 g) and alumina (1.5 g), stirred for 5 minutes and filtered hot. The clear solution was seeded with crystals obtained as in Example 1 and cooled to 0° for 18 hours. The white crystalline solid was filtered off and the wet product slurried in water (20 ml). The solid was filtered off, washed with water and dried to give the hydrochloride salt as the hemihydrate (7.9 g, 74.1%).

The $^1$H-n.m.r. spectrum was the same as that of the Example 4 product.

EXAMPLE 7

(−)-trans-4-(4'-Fluorophenyl)-3-(3',4'-methylenedioxyphenoxymethyl)-piperidine hydrochloride (−)-trans-4-(4'-Fluorophenyl)-3-(3',4'-methylenedioxyphenoxymethyl)-N-methylpiperidine (10 g) was dissolved in 45 ml of sodium dried toluene and the solution cooled to 5°. α-Chloroethyl chloroformate (3.22 ml) in 5 ml of dry toluene was added to the cold solution over 15 minutes. The mixture was stirred for 18 hours and methanol (15 ml) was added to the mixture. The solution was stirred for 12 hours at ambient temperature. The solvent was then distilled off in vacuo and the residue dissolved in hot isopropyl alcohol (60 ml). The hot solution was treated with charcoal (2 g) and alumina (1.5 g), stirred for 5 minutes, filtered, seeded with crystals obtained as in Example 1 and cooled to 0° for 18 hours. The white crystalline solid was filtered off, washed with a little isopropyl alcohol and the solid slurried in water (20 ml). The solid was filtered off, washed with water and dried to give the hydrochloride salt as the hemihydrate (9.8 g, 92%).

The $^1$H-n.m.r. spectrum was identical to that of the Example 4 product.

EXAMPLE 8

(−)-trans-4-(4'-Fluorophenyl)-3-(3'4'-methylenedioxyphenoxymethyl)-piperidine hydrochloride (paroxetine hydrochloride)

Crude (−)-trans-4-(4'-fluorophenyl)-3-(3'4'-methylenedioxyphenoxymethyl) piperidine (0.341 kg) is dissolved in diethyl ether (3.5 liters) and stirred with aluminium oxide (ca. 0.3 kg) for about 3 hours. Charcoal (15 g) and filter aid (celite, 15 g) are added and the mixture filtered through a layer of aluminium oxide, the filtered solids being washed with more ether. To the combined ether solutions is added a mixture of acetic acid (66 ml) and ether whereupon the acetate of (−)-trans-4-(4'-fluorophenyl)-3-(3'4'-methylenedioxyphenoxymethyl) piperidine crystallises and is filtered off, washed with ether and dried.

The acetate salt is dissolved in isopropanol (2.4 liters) and treated with a mixture of concentrated hydrochloric acid (75 ml) and more isopropanol. After standing at about 0° C. for about 16 hours, the crystals of the hydrochloride salt containing isopropanol (needles) are filtered off and dried. The salt is stirred in distilled water (0.5 liters) for about 20 minutes, filtered off and dried, giving (−)-trans-4-(4'-fluorophenyl)-3-(3'4'-methylenedioxyphenoxymethyl) piperidine hydrochloride anhydrate (platelets m.p. 118° C.). IR(Nujol Mull) $\nu$ 890, 1200, 1490, 3400, 3640 cm$^{-1}$.

Samples of the anhydrate were compressed at approximately 750 MNm$^{-2}$ and approximately 375 MNm$^{-2}$ for periods of about 2 minutes. The former underwent 45% conversion to the hemihydrate, whilst the latter remained unchanged.

Upon reexamining the samples after storage for several days, it was seen that the former sample had undergone complete conversion to the hemihydrate, whilst the latter sample had undergone about 50% conversion.

After a further week, the conversion of the latter sample was almost complete.

We claim:

1. Crystalline paroxetine hydrochloride hemihydrate.

2. Crystalline paroxetine hydrochloride hemihydrate in substantially pure form.

3. Crystalline paroxetine hydrochloride hemihydrate, having substantially the same X-ray diffractogram as set out in FIG. 1, substantially the same IR spectrum, in a Nujol mull, as set out in FIG. 2, and substantially the same DSC profile as set out in FIG. 3.

4. A process for the preparation of crystalline paroxetine hydrochloride hemihydrate, which process comprises forming a solution of paroxetine hydrochloride and crystallizing said hemihydrate from solution by precipitation or recrystallization.

5. An anti-depressant pharmaceutical composition comprising an effective anti-depressant amount of crystalline paroxetine hydrochloride hemihydrate and a pharmaceutically acceptable carrier.

6. A method of treatment of depression in mammals, which method comprises administering an effective amount of crystalline paroxetine hydrochloride hemihydrate.

* * * * *

UNITED STATES PATENT AND TRADEMARK OFFICE
CERTIFICATE OF CORRECTION

PATENT NO. : 4,721,723

DATED : January 26, 1988

INVENTOR(S) : Barnes et al.

It is certified that error appears in the above-identified patent and that said Letters Patent is hereby corrected as shown below:

Column 1, lines 13-14, "(4'-fluorophenyl) 3-(3'4'-methylenedioxyphenoxymethyl)-piperidine" should be -- (4'fluorophenyl)-3-(3',4'-methylenedioxyphenoxymethyl)piperidine --.

Column 2, line 24, "appropiate" should be -- appropriate --;

line 43, "water immiscible should be -- water-immiscible --;

line 44, "water miscible" should be -- water-miscible --;

line 63, "recrystallizatation" should be -- recrystallization --.

Column 6, line 52, "3'4'" should be -- 3',4' --;

line 53, "phenoxymethyl)-piperidine" should be -- phenoxymethyl)piperidine --;

line 56, "3'4'" should be -- 3',4' --;

line 65, "hyirochloric" should be -- hydrochloric --.

Column 7, line 7, "3'4'" should be -- 3',4' --;

line 16, "(15. 0ml)" should be -- (15.0ml) --;

line 36, "(5. 0ml)" should be -- (5.0ml) --;

UNITED STATES PATENT AND TRADEMARK OFFICE
CERTIFICATE OF CORRECTION

PATENT NO. : 4,721,723

DATED : January 26, 1988          Page 2 of 3

INVENTOR(S) : Barnes et al.

It is certified that error appears in the above-identified patent and that said Letters Patent is hereby corrected as shown below:

lines 42-43, "(3',4'-methylene-dioxyphenoxymethyl)-piperidine" should be -- (3',4'-methylenedioxyphenoxymethyl)piperidine --;

line 49, "dioxy-phenoxy) methyl-N- piperidine" should be -- dioxyphenoxymethyl)-N-methyl-piperidine --;

line 63, "isoprOpyl" should be -- isopropyl --.

Column 8, line 37, "phenoxymethyl-piperidine" should be -- phenoxymethyl)piperidine --;

line 42, "(3+,4'" should be -- 3-(3',4' --;

line 49, "phenoxymethyl)-piperidine" should be -- phenoxymethyl)piperidine --.

Column 9, line 10, "phenoxymethyl)-piperidine" should be -- phenoxymethyl)piperidine --;

line 34, "3'4'" should be -- 3',4' --;

line 35, "phenoxymethyl)-piperidine" should be -- phenoxymethyl)piperidine --;

line 38, "3'4'" should be -- 3',4' --;

line 39, "methylenedioxyphenoxymethyl) piperidine" should be -- methylenedioxyphenoxymethyl)piperidine --;

line 47, "3'4'" should be -- 3',4' --.

UNITED STATES PATENT AND TRADEMARK OFFICE
CERTIFICATE OF CORRECTION

PATENT NO. : 4,721,723
DATED : January 26, 1988
INVENTOR(S) : Barnes et al.

It is certified that error appears in the above-identified patent and that said Letters Patent is hereby corrected as shown below:

```
Column 10, line 1, "phenoxymethyl) piperidine" should be
-- phenoxymethyl)piperidine --;

line 10, "3'4'" should be -- 3',4' --;

line 11, "methylenedioxyphenoxymethyl) piperidine"
should be -- methylenedioxyphenoxymethyl)piperidine --.
```

Signed and Sealed this

Second Day of January, 1990

Attest:

JEFFREY M. SAMUELS

*Attesting Officer*    *Acting Commissioner of Patents and Trademarks*

UNITED STATES PATENT AND TRADEMARK OFFICE

CERTIFICATE EXTENDING PATENT TERM
UNDER 35 U.S.C. § 156

PATENT NO.:     4,721,723

DATED:          January 26, 1988

INVENTORS:      Roger D. Barnes et al.

PATENT OWNER:   Beecham Group p.l.c.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

702 DAYS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
    Commissioner of Patents and Trademarks